United States Patent [19]

Shiraishi

[11] Patent Number: 4,956,559

[45] Date of Patent: * Sep. 11, 1990

[54] METHOD OF DETECTING RADIOACTIVE SUBSTANCE

[75] Inventor: Hisashi Shiraishi, Minami-ashigara, Japan

[73] Assignee: Fuji Photo Film Co., Ltd., Minami-ashigara, Japan

[ * ] Notice: The portion of the term of this patent subsequent to Nov. 14, 2006 has been disclaimed.

[21] Appl. No.: 6,925

[22] Filed: Jan. 27, 1987

Related U.S. Application Data

[63] Continuation of Ser. No. 804,323, Dec. 4, 1985, abandoned, which is a continuation of Ser. No. 614,635, May 29, 1984, abandoned.

[30] Foreign Application Priority Data

May 27, 1983 [JP] Japan ................................. 58-93600
Jun. 10, 1983 [JP] Japan ................................ 58-103634
Jun. 10, 1983 [JP] Japan ................................ 58-103635

[51] Int. Cl.$^5$ ..................... G01T 7/02; G01T 1/167
[52] U.S. Cl. ................................ 250/484.1; 250/364; 250/327.2
[58] Field of Search ................... 250/327.2, 484.1, 364

[56] References Cited

U.S. PATENT DOCUMENTS

| | | | |
|---|---|---|---|
| 3,134,018 | 5/1964 | Schranz | 250/364 |
| 3,288,995 | 11/1966 | Demorest | 250/304 |
| 4,127,499 | 11/1978 | Chen et al. | 250/483.1 |
| 4,484,073 | 11/1984 | Ohara et al. | 250/337 |
| 4,507,562 | 3/1985 | Gasiot et al. | 250/473.1 |
| 4,562,158 | 12/1985 | Schellenberg | 250/483.1 |

FOREIGN PATENT DOCUMENTS

| | | | |
|---|---|---|---|
| 1241001 | 5/1967 | Fed. Rep. of Germany | 250/367 |
| 13381 | 1/1982 | Japan | 250/364 |
| 174877 | 10/1982 | Japan | 250/327.2 |

Primary Examiner—Carolyn E. Fields
Attorney, Agent, or Firm—Sixbey, Friedman, Leedom & Ferguson

[57] ABSTRACT

A method of detecting radioactive substance in a liquid sample which comprises steps of:
(1) supplying a radiation-measuring instrument containing a stimulable phosphor with the liquid sample continuously or intermittently;
(2) keeping said measuring instrument in contact with the liquid sample for a given period of time to cause the instrument to absorb at least a portion of radiation energy emitted by the radioactive substance in said liquid sample; and
(3) irradiating said measuring instrument with an electromagnetic wave to release the radiation energy stored in the instrument as stimulated emission, and photoelectrically detecting the stimulated emission to measure radioactivity of said liquid sample sequentially.

The method is particularly useful when employed in conjunction with liquid chromatography.

30 Claims, 2 Drawing Sheets

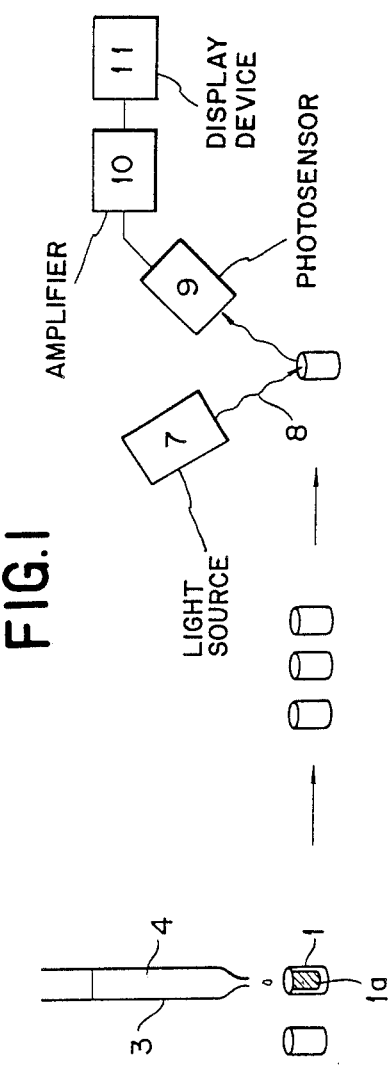
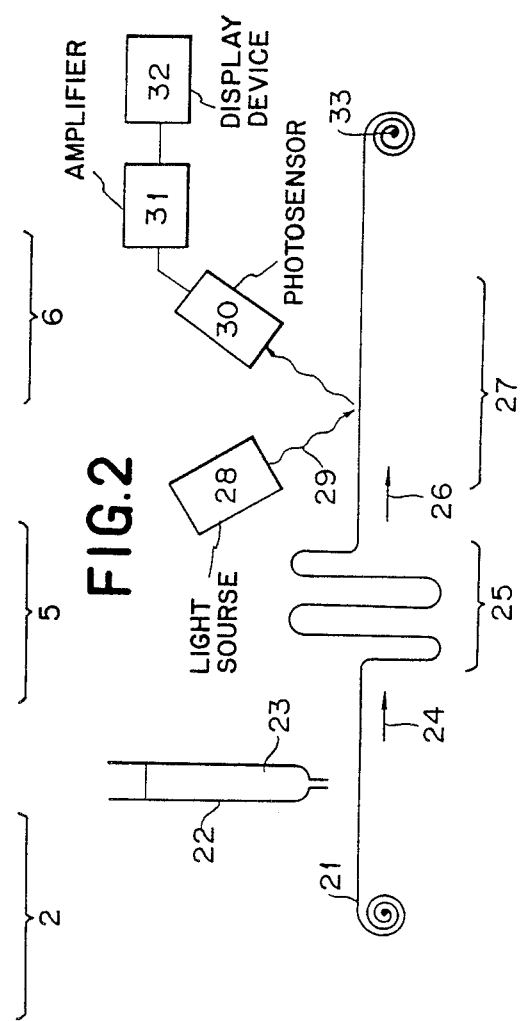

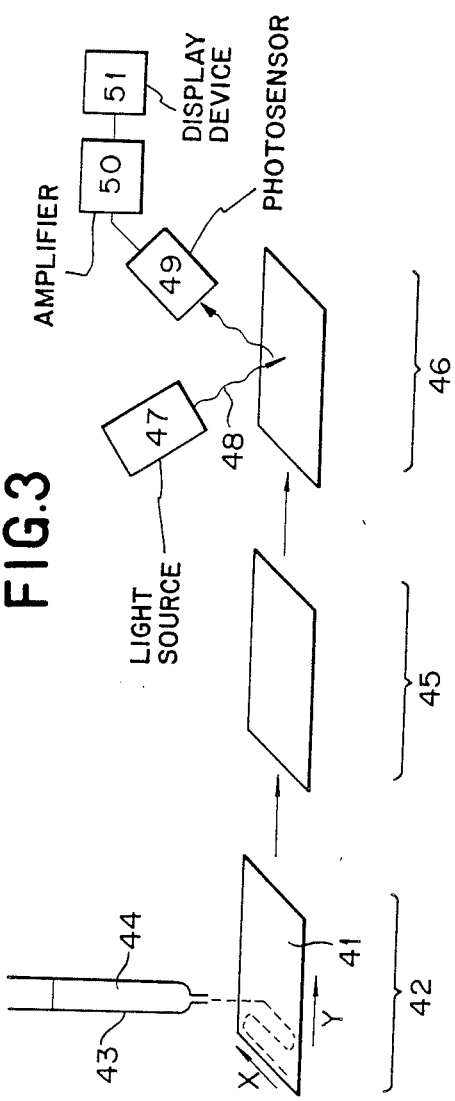
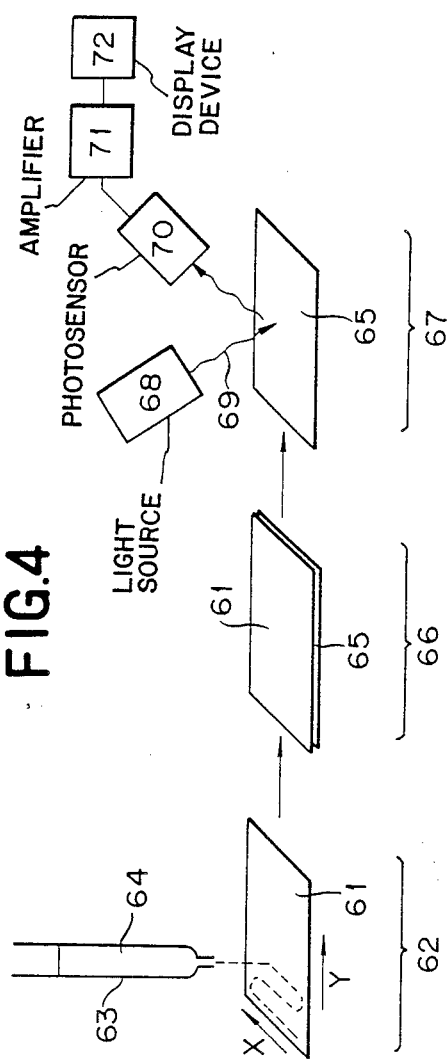

METHOD OF DETECTING RADIOACTIVE SUBSTANCE

This is a continuation of application Ser. No. 804,323, filed Dec. 4, 1985, which in turn is a continuation of Ser. No. 614,635 filed May 29, 1984, both now abandoned.

BACKGROUND OF THE INVENTION

1. Field of the Invention

The present invention relates to a method of detecting radioactive substance, and more particularly, to a method of detecting radioactive substance utilizing a stimulable phosphor.

2. Description of the Prior Art

Heretofore, as a method of measuring a radiation emitted by a liquid sample for detecting a radioactive substance (substance containing a radioisotope) contained therein, there are well known a liquid scintillation counting method wherein the radiation from the sample is converted into fluorescence to be detected by adding to the sample a liquid scintillator composed of a solute (fluorescent agent) dissolved in an organic solvent. In this method, the radioactivity of the radioactive substance contained in the sample is measured by causing the scintillator to absorb at least a portion of radiation energy emitted by the radioactive substance and detecting light (fluorescence) emitted by the scintillator.

The liquid scintillation counting method can be applied to the case where a liquid sample containing a radioactive substance can be continuously or intermittently supplied. The measurement of a radiation emitted by the sample is carried out by collecting a given amount of the sample and adding the liquid scintillator thereinto.

As a method for separation analysis, for example, there is known liquid chromatography wherein a sample solution is introduced into a column packed with a filler such as an adsorbent, an appropriate solvent is then supplied therethrough to develop the sample, and components in the sample are subsequently allowed to flow out from the column and collected. The liquid chromatography can be used for the separation of a sample containing radioactive substance, and the separation and identification of the radioactive substance are conducted by measuring a radiation emitted by an eluate collected through the operation of the liquid chromatography.

More in detail, the separation and identification of a radioactive substance in a sample are conducted by collecting the sample containing the radioactive substance which is separated and developed in the liquid chromatography with a fraction collector, adding a liquid scintillator to each fraction, and then detecting light emitted by the scintillator with a photomultiplier to convert it into an electric pulse and counting the electric pulse to measure the radiation dose of each fraction.

The above-described liquid scintillation counting method has such an advantage that the radioactivity can be detected even when a radiation from a radioactive substance are weak ones such as $\alpha$-rays and $\beta$-rays, and is a useful means for measuring the radioactivity of the liquid sample.

The mechanism of scintillation in the liquid scintillation counting method is described as follows: A molecule of a solvent in which a solute (fluorescent agent) is dissolved is initialy excited by a radiation emitted by a radioactive substance in a liquid sample, and then a solute molecule (scintillator) is excited through impingement of the excited solvent molecule on the solute molecule, or the like. In the course of transferring of the radiation energy from the solvent molecule to the solute molecule, there occur other phenomena such that the energy is transferred between the solvent molecules by interaction between the solvent molecule in the excited state and that in the ground state, or that the energy is transferred from the solvent molecule in the excited state to the other solute molecule than a scintillator by interaction therebetween before the scintillator is excited. The transfer of energy takes place not only through the interaction between molecules such as impingement, but also through such a phenomenon that the scintillator absorbs light emitted by the excited solvent molecule or other excited solute molecule.

However, in the course of the energy-transfer procedure, there also occurs such a quenching phenomenon that the excitation energy is absorbed by a portion of the solvent molecules or other solute molecules so as to be converted into heat, etc., or that the light emitted by the scintillator is absorbed by a light-absorbing substance contained in the sample.

The liquid scintillator, which is essential to said liquid scintillation counting method, is expensive and has to be isolated and refined to re-use it. Usually, it is difficult to recover the scintillator in a high purity so that it is not generally re-used and the measuring cost is increased thereby. Further, there are problems in handling thereof. For example, the used scintillator containing the radioisotope may cause a problem in the disposal stage such as environmental pollution.

Other problems reside in that the solvents allowed to use in conjunction the solutes (fluorescent agent) are generally limited to certain organic solvents so that there is difficulty in choosing a solvent for a sample, and specific procedure has to be taken in preparing a sample in the case that the sample is sparingly soluble in the solvent.

Since the scintillation mechanism of the liquid scintillator is complicated as stated above, the counting efficiency (that is, intensity of radioactivity to be detected) is apt to decrease by the quenching effect due to impurities contained in a sample or of the sample per se. For example, light emitted by the scintillator is liable to be quenched by the oxygen dissolved in the liquid scintillator, or to be absorbed (i.e. quenched) by a colorant in the case that the sample solution is colored thereby. In the case that a sample is sparingly soluble, it is not easy to prepare a sample solution in a homogeneous phase, and the unhomogeneous phase thereof causes internal absorption of a radiation emitted from the sample. For this reason, it is necessary to accurately determine the counting efficiency of the sample by making correction for quenching caused by the above-mentioned various phenomena, and this makes measuring procedure more complicated. Further, there is a disadvantage that it is substantially difficult to accurately measure the radioactivity of the sample even if the correction for quenching is made.

In order to prevent the counting efficiency from being lowered by quenching effect of contaminants, impurities and colored substances contained in the sample, the sample has to be carefully prepared, and high skill and much experience are required for the operators. The pretreatment of the sample to remove the contaminants is of importance to the measuring procedure.

In the conventional scintillation counting method, the measurement of radioactivity of a sample is conducted in a real time. Namely, it is necessary to continuously measure light emitted by the scintillator for a given time (for example, for several minutes to several ten minutes) after the sample is introduced into the scintillator solution. If the intensity of radiation from the sample is low, the measuring time (i.e., counting time) extends to a long time so that it can be hardly said that the measuring efficiency and the handling efficiency of measuring apparatus are sufficiently high. Therefore, in the case that a great number of samples are involved as described above, it is difficult to treat such a great number of samples once and the waiting period accordingly extends for many hours so that it disadvantageously takes a long time until the results are obtained. Particularly, in the case that the half-life of radioisotope in the sample is short, it becomes difficult to measure the radioactivity thereof. Further, in the case that the radiation intensity is low, the measurement becomes more difficult. This means that an apparatus (for example, dark current drift of photomultiplier) to be used must be stable over a long period of time. To keep the stability of apparatus, an expensive apparatus becomes necessary, or much skill and experience to adjust the apparatus are required.

Further, when the conventional liquid scintillation counting method is applied to a liquid sample containing a radioactive substance which is supplied continuously or intermittently from the above liquid chromatography, the radioactivity must be detected for every fraction by collecting the sample (which has been separated and developed in the liquid chromatography) by means of a fraction collector composed of a plurality of measuring containers (vials), and then measuring the radiation dose of each container with a scintillation counter.

Accordingly, in order to separate and identify the radioactive substance in the sample with higher accuracy by detecting the radioactivity of the separated and developed sample, it is required to use a greater number of measuring containers as the fraction collector. This means that the measuring procedures for collecting the sample solution and detecting the radioactivity are made complicated.

SUMMARY OF THE INVENTION

The present inventor has made studies to solve the above-mentioned problems associated with the conventional liquid scintillation counting method which has been employed for measuring radioactivity of a liquid sample containing a radioactive substance and being continuously or intermittently supplied, and has found that said problems can be solved or reduced by employing a method which comprises collecting the sample in or on a radiation-measuring instrument containing a stimulable phosphor and measuring radiation energy stored in the measuring instrument by detecting stimulated emission therefrom.

The present invention provides a method of detecting radioactive substance in a liquid sample which comprises steps of:

(1) supplying a radiation-measuring instrument containing a stimulable phosphor with the liquid sample continuously or intermittently;

(2) keeping said measuring instrument in contact with the liquid sample for a given period of time to cause the instrument to absorb at least a portion of radiation energy emitted by the radioactive substance in said liquid sample; and (3) irradiating said measuring instrument with an electromagnetic wave to release the radiation energy stored in the instrument as stimulated emission, and photoelectrically detecting the stimulated emission to measure radioactivity of said liquid sample sequentially.

Further, the present inventor has found that the above-described problems which particularly encounters in the liquid chromatography of a liquid sample containing a radioactive substance can be solved or reduced by employing one of the following methods:

(I) a method using a number of measuring containers with a built-in stimulable phosphor, which comprises sequentially introducing the liquid sample into a number of measuring containers and then measuring radiation energy stored in the measuring containers by detecting stimulated emission therefrom, (II) a method using a continuous-length measuring instrument (i.e., a measuring means in the form of a continuous form) containing a stimulable phosphor therein, which comprises continuously supplying the liquid sample onto the measuring instrument and then measuring radiation energy stored in the measuring instrument by detecting stimulated emission therefrom, or (III) a method using a sheet-form measuring instrument comprising a stimulable phosphor member containing a stimulable phosphor therein and a liquid-retaining member, both members being integrated with or separated from each other, which comprises continuously supplying the liquid sample to the measuring instrument and then measuring radiation energy stored in the measuring instrument by detecting stimulated emission therefrom.

The present invention provides a method of detecting radioactive substance in a liquid sample treated in liquid chormatography which comprises steps of:

(1) sequentially setting a plurality of measuring containers with a built-in stimulable phosphor under a sample supplier having a liquid sample, and supplying said liquid sample continuously or intermittently into said measuring containers from the sample supplier;

(2) keeping each of said plural measuring containers in contact with the liquid sample for a given period of time to cause the container to absorb at least a portion of radiation energy emitted by the radioactive substance in said liquid sample; and (3) irradiating each of said plural measuring containers with an electromagnetic wave to release the radiation energy stored in the container as stimulated emission, and photoelectrically detecting the stimulated emission to measure radioactivity of said liquid sample sequentially.

The present invention further provides methods of detecting radioactive substance in a liquid sample treated in liquid chromatography, using said continuous-length measuring instrument or said sheet-form measuring instrument in place of the above-mentioned plural measuring containers.

In the present invention, the radiation-measuring instrument involves not only a single element (such as continuous-length instrument or sheet-form instrument) but also a number of elements (such as containers). In the case of the instrument comprising a number of elements, a liquid sample to be measured is divided among said elements and each component of the sample supplied into each element is subjected to the measurement.

BRIEF DESCRIPTION OF DRAWINGS

FIGS. 1 to 4 are schematic views showing embodiments of radiation-measuring systems for detecting radioactive substance contained in a liquid sample which is continuously supplied dropwise in liquid chromatography.

DETAILED DESCRIPTION OF THE INVENTION

The stimulable phosphor used in the present invention has the property of emitting light (giving stimulated emission) when excited with an electromagnetic wave (stimulating rays) such as visible light or infrared rays after absorbing a radiation. Therefore, the radioactivity of a sample containing a radioactive substance can be measured in such a manner that the sample is introduced to the radiation-measuring instrument containing the stimulable phosphor therein (e.g., measuring container, continuous-length measuring instrument, sheet-form measuring instrument) to cause the measuring instrument to absorb a radiation emitted by the radioactive substance, the measuring instrument is irradiated with the stimulating rays to release the radiation energy stored in the instrument in proportion to the applied radiation dose as stimulated emission, and the stimulated emission is photoelectrically read out (detected) and converted into an electrical signal.

In the present invention, the stimulable phosphor contained in the radiation-measuring instrument gives stimulated emission instantaneously and the photometric time of the emission can be set irrespectively of the radiation intensity of a sample, so that the read-out operation after introducing the sample to the measuring instrument to allow the instrument to store the radiation energy emitted by the sample takes such a short time as from several seconds to several tens seconds. Thus, the measuring time can be shortened.

According to the methods of the present invention, the conventional scintillator is not required in the measurement of the radioactivity of a sample, and the operation of mixing (dissolving or suspending) the scintillator with the sample in a container is not either required, although said operation has to be performed in the conventional liquid scintillation counting method is not required. The measurement can be made merely by introducing the sample containing a radioactive substance to a radiation-measuring instrument having a stimulable phosphor. After using the measuring instrument, it is not necessary to separate the phosphor from the sample and to refine it in the methods of the present invention, so that the measuring instrument can be repeatedly used only by removing the sample therefrom and erasing the energy remaining therein under irradiation with an appropriate light, and the cost for one measurement can be reduced. The measuring instrument is very easy to handle, because it can be made of plastic material, etc.

A solvent is not necessarily employed in the present invention, which is different from the conventional liquid scintillation counting method. That is, the selection of a solvent and the preparation of a sample solution required in the use of the liquid scintillator are not always required in the method of the invention. Further, the above-mentioned quenching phenomena, particularly such as the phenomenon of quenching of the emitted light does not occur in the present invention. It is not necessary to make complicated quenching correction (determination of counting efficiency) for measuring the radioactivity of the sample, and the radioactivity thereof can be accurately measured without being greatly influenced by measuring conditions, etc. Accordingly, the measuring operation is simplified in this respect.

Particularly, since it is not necessary to remove impurities, etc. contained in the sample, the pretreatment of the sample as stated hereinbefore is not required, and much skill and attention based on the experience are not required for the preparation of the sample. The measurement of the radioactivity of the sample can be easily made further by this feature.

Specifically, the method of the present invention using the measuring container containing a stimulable phosphor enables to carry out the radiation energy-storing operation and the read-out operation independently, by removing the sample from the container after storing the radiation energy radiating therefrom in the container. The plural measuring containers can be read out together, and this also makes the measuring time shortened and the measuring procedure simplified.

Therefore, a great number of samples can be measured in one lot so that the working efficiency of the apparatus is increased, and the number of the measurement per a unit time can be increased. Further, the storing operation for a great number of samples can be simultaneously made using a plurality of the measuring containers, that is, the measurement of these samples can be made with high accuracy under the same conditions (measuring time, temperature, etc.). This means that the radioactivities of a great number of samples can be measured with high accuracy under the same conditions even when a radioisotope having a short half-life and a feeble radiation is involved. Further, when a plurality of the measuring containers are used with only one measuring apparatus in the present invention, the measuring efficiency can become substantially equal to that obtained in the case that a plurality of measuring apparatuses are used together in the conventional method.

It is furthermore possible to automate not only the operation for setting the plural measuring containers under a sample supplier and introducing the sample thereto, but also the operation for storing the radiation given by the sample therein and reading out of the radiation energy stored therein, so that the working efficiency of measurement can be more enhanced.

In another method of the present invention using the continuous-length measuring instrument containing a stimulable phosphor therein, a radiation emitted by a liquid sample can be continuously absorbed by the measuring instrument by moving the instrument in its lengthwise direction and allowing the sample to drop or flow down continuously or intermittently on the moving instrument to deposit the sample thereon. The radiation energy stored in the measuring intrument can be sequentially detected in the form of stimulated emission by irradiating the measuring instrument with stimulating rays. Therefore, it is possible to separate and identify a radioactive substance with high accuracy by sequentially detecting the radioactive substance in the sample which has been separated and developed in the liquid chromatography.

In the conventional method, a scintillator is added to each container after collecting a liquid sample with a fraction collector, and the radioactivity of each fraction is measured by a scintillation counter. Thus, the collecting operation of the sample solution and the measuring operation of radioactivity are completely separated from each other. According to the method of the present invention, it is possible to carry out both the operations in one stage (on-line) by moving the continuous-length measuring instrument containing the stimulable phosphor in the lengthwise direction to continuously deposit the sample thereon and subsequently transferring said instrument to subject it to the read-out operation of radiation energy stored therein. In this respect, the measuring time can be shortened and measuring procedure can be greatly simplified.

Further, it is possible to automate the moving operation of the continuous-length measuring instrument, the depositing operation of the sample on the instrument, the storing operation of radiation energy from the sample into the instrument, and the read-out operation of the radiation energy stored in therein, whereby workability can be further improved.

The continuous-length measuring instrument employed in the present invention can increase the adsorbing ability for liquid sample (e.g., permeability of sample), when the measuring instrument is in the form of a yarn or a fabric, so that a radiation from the sample can be efficiently absorbed by the stimulable phosphor contained in the instrument.

In the other method of the present invention using a sheet-form measuring instrument comprising a stimulable phosphor member and a liquid-retaining member, a radiation emitted by a liquid sample held by the liquid-retaining member can be continuously absorbed by the stimulable phosphor member, by moving the instrument in a suitable way and allowing the sample to drop or flow down continuously or intermittently on the moving instrument to deposit the sample on the liquid-retaining member. The radiation energy stored in the stimulable phosphor member of the measuring instrument can be sequentially detected in the form of stimulated emission by irradiating the measuring instrument with stimulating rays. Therefore, it is possible to separate and identify a radioactive substance with high accuracy by sequentially detecting the radioactive substance in the sample which is separated and developed in a liquid chromatography.

More in detail, the sheet-form measuring instrument employed in the present invention has both functions such as a function capable of retaining a liquid sample and a function capable of storing radiation energy given by the sample and releasing it as stimulated emission. The measuring instrument may be in an integrated form comprising a stimulable phosphor member and a liquid-retaining member provided thereon, or in a separated form comprising both members which are arranged independently. Especially, in the case of separated instrument, it is possible to carry out separately the depositing operation of sample on the measuring instrument (i.e., the liquid-retaining member), the storing operation of radiation energy from the sample in the liquid-retaining member into the stimulable phosphor member by the superposition thereof, and the read-out operation of the instrument (i.e., the stimulable phosphor member), so that the plural stimulable phosphor members can be read out together. Further, the stimulable phosphor member can be repeatedly used by erasing the remaining energy under irradiation with an appropriate light.

The deposition of the liquid sample on the liquid-retaining member of the sheet-form measuring instrument can be, for example, conducted as follows: The measuring instrument is horizontally placed under a sample supplier such as a column. Then the measuring instrument is horizontally moved in one direction (hereinafter referred to as X-direction), while the liquid sample from the supplier is allowed to drop or flow down continuously or intermittently, whereby the liquid sample is held and adsorbed in the form of a spot or band on the liquid-retaining member. Just before one end of the sheet-form measuring instrument exceeds the point onto which the sample drops, the direction of movement of the measuring instrument is altered in such a manner that the instrument moves still horizontally but shifts slightly to move to a direction perpendicular to the X-direction (hereinafter referred to as Y-direction), and then the instrument is moved in the X-direction reversely. In this way, the sheet-form measuring instrument is moved in conjunction with slight shift in the Y-direction and repeatedly going to and from in the X-direction, so that the sample can be retained in the form of a continuous or discontinuous band on the liquid-retaining member. The above-described moving operation of the measuring instrument is illustrated to merely show one example. It is apparent that other modifications can be made within the scope of the present invention.

The following illustrates the radiation-measuring instrument employed in the present invention in detail.

The stimulable phosphor, as described hereinbefore, gives stimulated emission when excited with stimulating rays after exposure to a radiation. From the viewpoint of practical use, the stimulable phosphor is desired to give stimulated emission in the wavelength region of 300–500 nm when excited with stimulating rays in the wavelength region of 400–850 nm.

Examples of the stimulable phosphor employable in the method of the present invention include:

SrS:Ce,Sm, SrS:Eu,Sm, ThO$_2$:Er, and La$_2$O$_2$S:Eu,Sm, as described in U.S. Pat. No. 3,859,527;

ZnS:Cu,Pb, BaO.xAl$_2$O$_3$:Eu, in which x is a number satisfying the condition of $0.8 \leq x \leq 10$, and M$^{2+}$O.xSiO$_2$:A, in which M$^{2+}$ is at least one divalent metal selected from the group consisting of Mg, Ca, Sr, Zn, Cd and Ba, A is at least one element selected from the group consisting of Ce, Tb, Eu, Tm, Pb, Tl, Bi and Mn, and x is a number satisfying the condition of $0.5 \leq x \leq 2.5$, as described in U.S. Pat. No. 4,326,078;

(Ba$_{1-x-y}$,Mg$_x$,Ca$_y$)FX:aEu$^{2+}$, in which X is at least one element selected from the group consisting of Cl and Br, x and y are numbers satisfying the conditions of $0 < x+y \leq 0.6$, and $xy \neq 0$, and a is a number satisfying the condition of $10^{-6} \leq a \leq 5 \times 10^{-2}$, as described in Japanese Patent Provisional Publication No. 55(1980)-12143;

LnOX:xA, in which Ln is at least one element selected from the group consisting of La, Y, Gd and Lu, X is at least one element selected from the group consisting of Cl and Br, A is at least one element selected from the group consisting of Ce and Tb, and x is a number satisfying the condition of $0 < x < 0.1$, as described in the above-mentioned U.S. Pat. No. 4,236,078;

(Ba$_{1-x}$,M$^{II}_x$)FX:yA, in which M$^{II}$ is at least one divalent metal selected from the group consisting of Mg, Ca, Sr, Zn and Cd, X is at least one element selected from the group consisting of Cl, Br and I, A is at least one element selected from the group consisting of Eu, Tb, Ce, Tm, Dy, Pr, Ho, Nd, Yb and Er, and x and y are numbers satisfying the conditions of $0 \leq x \leq 0.6$ and $0 \leq y \leq 0.2$, respectively, as described in Japanese Patent Provisional Publication No. 55(1980)-12145;

$M^{II}FX \cdot xA:yLn$, in which $M^{II}$ is at least one element selected from the group consisting of Ba, Ca, Sr, Mg, Zn and Cd; A is at least one compound selected from the group consisting of BeO, MgO, CaO, SrO, BaO, ZnO, $Al_2O_3$, $Y_2O_3$, $La_2O_3$, $In_2O_3$, $SiO_2$, $TiO_2$, $ZrO_2$, $GeO_2$, $SnO_2$, $Nb_2O_5$, $Ta_2O_5$ and $ThO_2$; Ln is at least one element selected from the group consisting of Eu, Tb, Ce, Tm, Dy, Pr, Ho, Nd, Yb, Er, Sm and Gd; X is at least one element selected from the group consisting of Cl, Br and I; and x and y are numbers satisfying the conditions of $5 \times 10^{-5} \leq x \leq 0.5$ and $0 < y \leq 0.2$, respectively, as described in Japanese Patent Provisional Publication No. 55(1980)-160078;

$(Ba_{1-x},M^{II}_x)F_2 \cdot aBaX_2:yEu,zA$, in which $M^{II}$ is at least one element selected from the group consisting of Be, Mg, Ca, Sr, Zn and Cd; X is at least one element selected from the group consisting of Cl, Br and I; A is at least one element selected from the group consisting of Zr and Sc; and a, x, y and z are numbers satisfying the conditions of $0.5 \leq a \leq 1.25$, $0 \leq x \leq 1$, $10^{-6} \leq y \leq 2 \times 10^{-1}$, and $0 < z \leq 10^{-2}$, respectively, as described in Japanese Patent Provisional Publication No. 56(1981)-116777;

$(Ba_{1-x},M^{II}_x)F_2 \cdot aBaX_2:yEu,zB$, in which $M^{II}$ is at least one element selected from the group consisting of Be, Mg, Ca, Sr, Zn and Cd; X is at least one element selected from the group consisting of Cl, Br and I; and a, x, y and z are numbers satisfying the conditions of $0.5 \leq a \leq 1.25$, $0 \leq x \leq 1$, $10^{-6} \leq y \leq 2 \times 10^{-1}$, and $0 < z \leq 2 \times 10^{-1}$, respectively, as described in Japanese Patent Provisional Publication No. 57(1982)-23673;

$(Ba_{1-x},M^{II}_x)F_2 \cdot aBaX_2:yEu,zA$, in which $M^{II}$ is at least one element selected from the group consisting of Be, Mg, Ca, Sr, Zn and Cd; X is at least one element selected from the group consisting of Cl, Br and I; A is at least one element selected from the group consisting of As and Si; and a, x, y and z are numbers satisfying the conditions of $0.5 \leq a \leq 1.25$, $0 \leq x \leq 1$, $10^{-6} \leq y \leq 2 \times 10^{-1}$, and $0 < z \leq 5 \times 10^{-1}$, respectively, as described in Japanese Patent Provisional Publication No. 57(1982)-23675;

$M^{III}OX:xCe$, in which $M^{III}$ is at least one trivalent metal selected from the group consisting of Pr, Nd, Pm, Sm, Eu, Tb, Dy, Ho, Er, Tm, Yb, and Bi; X is at least one element selected from the group consisting of Cl and Br; and x is a number satisfying the condition of $0 < x < 0.1$, as described in Japanese Patent Provisional Publication No. 58(1983)-69281;

$Ba_{1-x}M_{x/2}L_{x/2}FX:yEu^{2+}$, in which M is at least one alkali metal selected from the group consisting of Li, Na, K, Rb and Cs; L is at least one trivalent metal selected from the group consisting of Sc, Y, La, Ce, Pr, Nd, Pm, Sm, Gd, Tb, Dy, Ho, Er, Tm, Yb, Lu, Al, Ga, In and Tl; X is at least one halogen selected from the group consisting of Cl, Br and I; and x and y are numbers satisfying the conditions of $10^{-2} \leq x \leq 0.5$ and $0 < y \leq 0.1$, respectively, as described in Japanese Patent Provisional Publication No. 58(1983)-206678;

$BaFX \cdot xA:yEu^{2+}$, in which X is at least one halogen selected from the group consisting of Cl, Br and I; A is at least one fired product of a tetrafluoroboric acid compound; and x and y are numbers satisfying the conditions of $10^{-6} \leq x \leq 0.1$ and $0 < y \leq 0.1$, respectively, as described in Japanese Patent Provisional Publication No. 59(1984)-27980;

$BaFX \cdot xA:yEu^{2+}$, in which X is at least one halogen selected from the group consisting of Cl, Br and I; A is at least one fired product of a hexafluoro compound selected from the group consisting of monovalent and divalent metal salts of hexafluoro silicic acid, hexafluoro titanic acid and hexafluoro zirconic acid; and x and y are numbers satisfying the conditions of $10^{-6} \leq x \leq 0.1$ and $0 < y \leq 0.1$, respectively, as described in Japanese Patent Provisional Publication No. 59(1984)-47289;

$BaFX \cdot xNaX':aEu^{2+}$, in which each of X and X' is at least one halogen selected from the group consisting of Cl, Br and I; and x and a are numbers satisfying the conditions of $0 < x \leq 2$ and $0 < a \leq 0.2$, respectively, as described in Japanese Patent Provisional Publication No. 59(1984)-56479;

$M^{II}FX \cdot xNaX':yEu^{2+}:zA$, in which $M^{II}$ is at least one alkaline earth metal selected from the group consisting of Ba, Sr and Ca; each of X and X' is at least one halogen selected from the group consisting of Cl, Br and I; A is at least one transition metal selected from the group consisting of V, Cr, Mn, Fe, Co and Ni; and x, y and z are numbers satisfying the conditions of $0 < x \leq 2$, $0 < y \leq 0.2$ and $0 < z \leq 10^{-2}$, respectively, as described in Japanese Patent Provisional Publication No. 59(1984)-56480; and $M^{II}FX \cdot aM^{I}X' \cdot bM'^{II}X''_2 \cdot cM^{III}X'''_3 \cdot xA:yEu^{2+}$, in which $M^{II}$ is at least one alkaline earth metal selected from the group consisting of Ba, Sr and Ca; $M^{I}$ is at least one alkali metal selected from the group consisting of Li, Na, K, Rb and Cs; $M'^{II}$ is at least one divalent metal selected from the group consisting of Be and Mg; $M^{III}$ is at least one trivalent metal selected from the group consisting of Al, Ga, In and Tl; A is at least one metal oxide; X is at least one halogen selected from the group consisting of Cl, Br and I; each of X', X'' and X''' is at least one halogen selected from the group consisting of F, Cl, Br and I; a, b and c are numbers satisfying the conditions of $0 \leq a \leq 2$, $0 \leq b \leq 10^{-2}$, $0 \leq c \leq 10^{-2}$ and $a+b+c \geq 10^{-6}$; and x and y are numbers satisfying the conditions of $0 < x \leq 0.5$ and $0 < y \leq 0.2$, respectively, as described in Japanese Patent Application No. 57(1982)-184455.

The above-described stimulable phosphors are given by no means to restrict the stimulable phosphor employable in the present invention. Any other phosphor can be also employed, provided that the phosphor gives stimulated emission when excited with stimulating rays after exposure to a radiation.

One embodiment of the radiation-measuring instrument containing a stimulable phosphor, namely a measuring container can be prepared using the above-mentioned phosphor, for example, in the following manner.

One of the measuring container employed in the present invention generally comprises a housing part for a sample and a lid part. The lid is not always necessary, and is employed as a need arises. The stimulable phosphor built in the container is not always contained in the whole portion of the container, and it may be contained within a part of the container such as a whole or portion of a wall, a bottom part, etc.

In the case that the surface area of the part having the built-in stimulable phosphor is increased for the measuring container, the ability of capturing of a radiation from a sample and the accuracy of measured value can be improved, and the detection of a trace amount of a radioactive substance in the sample or the detection of a substance exhibiting a low radiation intensity becomes possible. On the other hand, from the viewpoint of convenience of reading out the radiation energy, it is preferred to use a container wherein the stimulable phosphor is built in a part of the container. In such a case, it is desirable that the phosphor is built in a part which is to be in contact with the sample. Further, it is preferred to use a measuring container wherein the distance between the part having the built-in phosphor and the radioactive substance (radiation source) in the sample is as short as possible from the viewpoint of the range of radiation from the sample.

Therefore, it is desirable to choose the shape of the container depending upon the amount and radiation intensity of a sample to be measured and measuring conditions in the measurement of a radioactive substance in the present invention.

Example of materials of the measuring container employed in the present invention include glass, quartz and plastics such as polyethylene, polypropylene, nylon, polyfluoroethylene, etc.

The measuring container can be formed by incorporating the stimulable phosphor into the above-mentioned material. The size, thickness and shape of the measuring container, and the amount and area of the stimulable phosphor to be built in the container can be determined according to the conditions and amount of samples to be measured and the measuring conditions.

The measuring container may contain particulate stimulable phosphor dispersed in a binder.

Examples of the binder include: natural polymers such as proteins (e.g. gelatin), polysaccharides (e.g. dextran) and gum arabic; and synthetic polymers such as polyvinyl butyral, polyvinyl acetate, nitrocellulose, ethylcellulose, vinylidene chloride-vinyl chloride copolymer, polymethyl methacrylate, vinyl chloride-vinyl acetate copolymer, polyurethane, cellulose acetate butyrate, polyvinyl alcohol, and linear polyester. Particularly preferred are nitrocellulose, linear polyester, and a mixture of nitrocellulose and linear polyester.

Examples of the solvent employable for dispersing the stimulable phosphor particles in the binder include lower alcohols, chlorinated hydrocarbons, ketones, esters and ethers.

The ratio between the binder and the phosphor in the dispersion may vary according to the shape of container, the kind of hosphor employpaied, etc. Generally, the ratio therebetween is within the range of from 1:1 to 1:100 (binder:phosphor, by weight), preferably from 1:8 to 1:40.

The dispersion may contain a dispersing agent to assist the dispersibility of the phosphor particles therein, and also contain a variety of additives such as a plasticizer for increasing the bonding between the binder and the phosphor particles in the phosphor layer.

The measuring container may be a layer structure comprising a support made of a plastic material such as polyethylene terephthalate and a layer (phosphor layer) composed of a stimulable phosphor dispersed in a binder. Namely, the container may be prepared by heat-treating a sheet comprising a support and a phosphor layer to form a container.

Alternatively, the measuring container may be in a structure wherein a shaped product composed of a stimulable phosphor dispersed in a binder is put in a portion of the container composed of the aforementioned material. It is desirable that the detachable shaped product is covered with a transparent polymer material such as polyethylene or polyethylene terephthalate to protect chemically and physically the phosphor.

In the present invention, it is not always necessary to introduce a sample directly into the container. Another container (intra-container) is previously placed within the measuring container, and the sample is inserted into the intra-container.

Another embodiment of the radiation-measuring instrument employed in the present invention, namely a continuous-length measuring instrument can be included a tape produced from a material such as natural polymer, plastics or glass containing a stimulable phosphor; a yarn (e.g., twine) and a fabric produced from a fiber which is spinned out of said material.

The continuous-length measuring instrument can be prepared, for example, in the following manner.

The natural polymers and plastic materials can be employed among those employed as a binder of the measuring container as described above. The above-mentioned stimulable phosphor and the material are dissolved or suspended in an appropriate solvent (such as lower alcohol, chorinated hydrocarbon, ketone, ester or ether), or heat-treated to incorporate the phosphor in the material. The material containing the phosphor is then produced into a continuous-length form to obtain a measuring instrument containing the stimulable phosphor.

The measuring instrument may be covered with a protective film composed of a transparent polymer material such as polyethylene or polyethylene terephthalate to protect the instrument from chemical deteriolation and/or physical shock.

The diameter or width and the length of the obtained measuring instrument, and the amount of the phosphor to be incorporated therein can be suitably selected according to the amount and density of a sample and the measuring conditions.

The measuring instrument is preferable to have a liquid-adsorbing ability. The liquid-adsorbing ability can be imparted to the instrument not only by making it in a liquid-adsorbing structure such as a yarn or a fabric, but also by processing the surface of the instrument.

Examples of the method of imparting the liquid-adsorbing ability to the measuring instrument by the surface processing include methods of subjecting the surface of the shaped product (or protective film) to the following surface-activation treatments: a physical treatment such as a surface-roughing treatment; an electrical treatment such as corona discharge, high-frequency discharge, glow discharge or activated-plasma discharge; a treatment with ultraviolet rays or laser beam; a flame treatment; and an oxidation treatment with ozone; and the like. Also included are methods of providing the liquid-adsorbing layer on the surface of the shaped product. The liquid-adsorving layer can be made of a natural polymer having a hydrophilic or hydrophobic property; a synthesized polymer; porous polymer thereof; a paper such as filter paper; or a fibrous material (fabric) such as cellulose derivative, gauze, etc.

It is not necessary that the measuring instrument is processed all over the surface. For example, when the instrument is in the form of a tape, only one side thereof may be processed. Even when the instrument is composed of a yarn or a fabric, the above-mentioned surface-processing may be conducted to increase liquid-adsorbing aability.

It is particularly preferred that the measuring instrument employed in the present invention is a yarn or fabric which is made of a plastic fiber or glass fiber containing the stimulable phosphor, from the viewpoints of the adsorbing ability for a liquid sample, the reusability of the instrument and the automated continuous and repeated measurement.

However, the continuous-length measuring instrument employed in the invention is not restricted to the above-described ones, and any continuous-length measuring instruments can be employed, provided that the instrument contains a stimulable phosphor and is capable of retaining or adsorbing a liquid sample continuously, which is dropped or flowed down thereon.

The other embodiment of the radiation-measuring instrument employable in the present invention, namely, a sheet-form measuring instrument containing a stimulable phosphor basically comprises a stimulable phosphor member and a liquid-retaining member. The measuring instrument may be in an integrated form in which both members are combined or in a separated form in which both members are independentlly arranged each other.

The integrated measuring instrument comprises a stimulable phosphor member in the form of a phosphor layer containing a stimulable phosphor and a liquid-retaining member in the form of a liquid-retaining layer provided on said phosphor layer.

The phosphor layer can be prepared, for example, in the following manner: The dispersion as employed in the preparation of the above-mentioned measuring container is coated on a sheet such as glass plate, metal plate or plastic sheet to form a layer of coating dispersion. The coating procedure can be conducted by means of doctor blade, roll coater, knife coater, etc. Then, the coating dispersion applied to the sheet is heated slowly to dryness so as to complete the formation of a phosphor layer. The thickness of the phosphor layer is generally within the range of from 50 to 500 μm.

On the surface of the phosphor layer to receive a liquid-retaining layer, a transparent protective film may be provided to protect the phosphor layer chemically and physically. Examples of the protective film include cellulose acetate, polymethyl methacrylate, polyethylene terephthalate and polyethylene. The thickness of the protective film is within the range of from 0.1 to 20 μm.

On another surface of the phosphor layer, a support may be provided, which is made of a plastic material such as cellulose acetate, polyester, polyethylene terephthalate; a metallic sheet such as aluminum foil; or a paper such as baraita paper or resin-coated papaer. The support can be provided by directly forming the phosphor layer thereon or by fixing it onto the phosphor layer with an adhesive agent. In the case of reading out the measuring instrument from the support side, it is preferred that the support is made of a transparent plastic material. The provision of the support onto the phosphor layer can bring about the enhancement of the mechanical strength and durability of measuring instrument to be obtained.

The phosphor layer can be also prepared by depositing phosphor particles over the support through vacuum-depositing.

The liquid-retaining layer is then formed on the surface of the phosphor layer (or the surface of the protective film in the case that it is provided on the phosphor layer).

It is preferred that the liquid-retaining layer has such a function that when a liquid sample is spotted on said layer, the sample is spread on the surface of said layer in proportion to the spotted amount and at the same time, the sample is caused to soak through said layer so that a substantially uniform amount of the sample per the unit area of said layer can be held.

As materials for the liquid-retaining layer having such a function, there is used, for example, a porous structure capable of adsorbing and holding the liquid sample by physical mechanism such as capillarity. Examples of the porous structure include fibrous materials such as a paper (e.g., filter paper) and fabrics (e.g., gauze); and non-fibrous materials such as porous polymers, porous glass and glass-like materials. In addition, there may be used materials which can be swollen by a solvent of the sample solution, thereby can absorb the sample solution.

In the case that the solvent of sample solution is a hydrophilic one such as water, examples of the materials of the liquid-retaining layer include natural polymer materials such as gelatin, starch, agarose, cellulose, and their derivatives; and synthetic polymer materials such as synthetic copolymers resulting from the copolymerization of a hydrophilic monomer having a hydrophilic group such as hydroxyl group or carboxyl group with a hydrophobic monomer. In the case of a lipophilic solvent, examples of the material of the liquid-retaining layer include synthetic polymer materials such as nylon, polyethylene and polyester, in addition to those described above.

The formation of the liquid-retaining layer on the phosphor layer can be done, for example, by any of known layer-forming methods such as a method of coating the surface of the phosphor layer with a solution of the above material dissolved in water or other solvent, or a latex dispersion.

In order to prevent the deposited liquid sample from spreading in the lateral direction exceeding a given width, there may be provided partition having an appropriate size and shape made of an appropriate plastic or metal filament or lattice or net structure grid. The liquid-retaining layer may be composed of single layer or a plurality of layers in the laminated form. The thickness of the liquid-retaining layer varies depending on the kind and amount of a radioactive substance in the sample, the kind of the solvent of the sample, and is preferable within the range of about 1 μm to 10 mm.

When the measuring instrument is read out from the side of the liquid-retaining layer, it is preferred that said layer is transparent from the viewpoints of light-transmissivity for stimulating rays and stimulated emission.

Further, in order to increase adhesion between the liquid-retaining layer and the phosphor layer (or the protective film), the surface of the phosphor layer (or the protective film) may be subjected to various activation treatment. Examples of such activation treatments include chemical treatments with a reagent such as acid, alkali or etching agent, as well as such activation treatments as employed in the preparation of the continuous-length measuring instrument.

The side-surface of the sheet-form measuring instrument may be covered with a polymer covering material such as polyurethane or acrylic resin, to increase the mechanical strength of the obtained measuring instrument.

The sheet-form measuring instrument may be in an arbitrary form such as a quadrangle, a circle or an oval having an appropriate size according to the measuring conditions of measuring system, the amount and radioactivity of a sample, etc.

The separated sheet-form measuring instrument basically comprises a stimulable phosphor member in the form of a stimulable phosphor sheet and a liquid-retaining member in the form of a liquid-retaining support medium. The liquid-retaining support medium is to adsorb and hold a liquid sample and the stimulable phosphor sheet is to store the radiation energy emitted by the sample and then to release it as stimulated emission.

In the separation type instrument, the stimulable phosphor sheet has a basic structure comprising the above-described support and phosphor layer which is provided on the support and composed of a binder and a stimulable phosphor dispersed therein. Further, it is preferred that the above-mentioned protective film is provided on the opposite surface (surface not facing the support) of the phosphor layer to protect the phosphor layer from chemical deterioration or physical shock.

The liquid-retaining support medium which is the other structural member of the separated measuring instrument can be formed using the same materials as those used for the afore-mentioned liquid-retaining layer. A supporting auxiliary element such as a glass sheet or a plastic sheet may be provided on this liquid-retaining member.

The method for detecting a radioactive substance by using the radiation-measuring instrument containing a stimulable phosphor according to the present invention will be described, by referring to the accompanying drawings.

Samples to be measured in the present invention are liquid samples containing radioactive substances, which may be solutions or dispersions, and may be colored.

As radiations emitted by radioactive substances in the samples, any radiations such as α-rays, β-rays, γ-rays, proton beam, neutron beam, meson beam, cosmic rays and other rays can be measured. Namely, any radiations emitted by any radionuclides can be measured.

The detection of a radioactive substance in a liquid sample can be carried out using a number of the measuring containers containing a stimulable phosphor, for example, as follows:

FIG. 1 schematically illustrates an embodiment of a radiation-measuring system for detecting a radioactive substance present in a sample which is allowed to drop continuously.

In a sample-supplying section 2, a liquid sample 4 in a sample supplier 3 is allowed to drop from the bottom of the supplier onto a measuring container 1 containing a stimulable phosphor 1a, which is set under the sample supplier 1 so as to sequentially introduce a given amount of the liquid sample into the plural measuring containers.

In a radiation energy storage section 5, at least a portion of radiation energy emitted by a radioactive substance in the sample is absorbed by each of the measuring container 1 and stored therein. The storing time (exposure time) of radiation energy varies depending on the intensity of a radiation emitted by the radioactive substance in the sample, the concentration of said substance, the shape of the measuring container, the intensity of stimulated emission from the container, etc., but usually ranges from approximately 1 second to 1 minute.

In a read-out section 6, each of the measuring container 1 is then irradiated with stimulating rays 8 emitted by a light source 7. The measuring container 1 emits light (gives stimulated emission) being proportional to the radiation energy stored therein under irradiation with the stimulating rays. The emitted light enters a photosensor 9 such as photomultiplier. The photosensor is provided with such a filter that allows only light in the wavelength region of the stimulated emission to pass therethrough and cuts off light in the wavelength region of the stimulating rays, so as to detect only the stimulated emission. The emitted light detected by the photosensor 9 is converted into an electric signal, which is then amplified to an appropriate level by an amplifier 10 and input into a recording or displaying device 11.

On the device 11, the level of the electric signal corresponding to the radiation dose absorbed by the measuring container, for example, the counted value of an electric pulse is displayed as a digital value. As the recording or displaying device 11, various devices based on various systems can be employed, for example, a device for optically recording by scanning a photosensitive material with laser beam, etc., a device for electronically displaying on CRT, etc., a device for printing a radiation image displayed on CRT by means of a video printer, and a device for recording on a heat-sensitive recording material by using thermic rays.

It is possible that the intensity of radioactivity is calculated on the basis of the resulting digital value according to read-out efficiency (luminance efficiency of stimulated emission) previously input and the storing time of radiation energy, by providing a data processing circuit within the device 11. Further, by inputting the intensity of radioactivity per 1 mole of the radioactive substance, the amount or the concentration of the radioactive substance for each container can be calculated and then the resulting data can be displayed and recorded.

The detection of a radioactive substance in a liquid sample can be carried out in the following manner in the case of using the sheet-form measuring instrument containing a stimulable phosphor.

FIG. 2 schematically illustrates an embodiment of a radiation-measuring system for detecting a radioactive substance present in a sample which is allowed to drop continuously.

A liquid sample 23 in a sample supplier 22 is allowed to drop from the bottom of the supplier on a continuous-length measuring instrument 21 containing a stimulable phosphor. The measuring instrument 21 is moved in the direction of an arrow 24 and the sample-deposited part of the measuring instrument 21 enters a radiation energy-storage section 25.

In the radiation energy-storage section 25, at least a portion of the radiation energy emitted by a radioactive substance in the sample is absorbed by the measuring instrument 21 and stored therein. The storing time usually ranges from several seconds to several tens of seconds. Hence, the moving speed is so adjusted to coincide with the transit time through the storage section 25 with the storing time. If desired, the drying of the sample may be simultaneously conducted in the storage section 25 by warming the measuring instrument 21 and the like.

The sample-deposited part of the measuring instrument 21 leaving the storage section 25 is moved in the direction of an arrow 26 and enters a read-out section 27, where the sample-deposited part of the instrument 21 is irradiated with stimulating rays 29 radiating from a light source 28. It is preferred that the stimulating rays 29 has a beam diameter of at least a size corresponding to the width of the sample-deposited part in perpendicular to the moving direction.

When the sample-deposited part of the measuring instrument 21 is irradiated with stimulating rays, said part emits light proportional to the radiation energy stored therein. Then, the emitted light enters a photosensor 30, wherein the light is converted to an electric signal, and the electric signal is amplified by an amplifier 31 and input into a recording or displaying device 32 to record the intensity of radioactivity thereon, in the same manner as described above.

Thus, the radioactivity of the radioactive substance contained in the sample is obtained.

On the other hand, the measuring instrument 21 leaving the read-out section 27 is wound around a wind-up device 33 to hold it.

The detection of a radioactive substance in a liquid sample can be carried out in the following manner in the case of using the sheet-form measuring instrument containing a stimulable phosphor.

FIG. 3 schematically illustrates an embodiment of a radiation-measuring system employing the integrated instrument for detecting a radioactive substance present in a sample which is allowed to drop continuously.

In a sample-supplying (sample-depositing) section 42, a liquid sample 44 is allowed to drop from the bottom of a sample supplier 43 onto a liquid-retaining layer of an integrated measuring instrument 41. The measuring instrument 41 is moved in the direction of arrows X and Y as mentioned before, while allowing the liquid sample 44 to drop thereon. With the movement of the instrument 41, the sample is deposited on the instrument 41 in a continuous or discontinuous band form, adsorbed and held by the liquid-retaining layer thereof.

In a radiation energy-storage section 45, at least a portion of the radiation energy emitted by a radioactive substance in the sample held by the liquid-retaining layer of the measuring instrument 41 is absorbed by the phosphor layer of the measuring instrument 41, and stored therein. The storing time of radiation energy usually ranges from about 1 sec. to 1 min. The drying of the sample on the measuring instrument 41 may be simultaneously conducted in the storage section 45 by warming the instrument 41 or the like.

In a read-out section 46, the measuring instrument 41 is irradiated with stimulating rays 48 radiating from a light source 47. It is preferred that the stimulating rays 48 has a beam diameter of at least a size corresponding to the width of the band of the deposited sample. When the phosphor layer of the measuring instrument 41 is irradiated with stimulating rays, the phosphor layer emits light being proportional to the radiation energy stored therein. Then, the emitted light enters a photosensor 49, in which the light is converted to an electric signal, and the electric signal is amplified by an amplifier 50 and input into a recording or displaying device 51 to record the intensity of radioactivity thereon, in the same manner as described above.

Thus, the radioactivity of the radioactive substance contained in the sample is determined.

In the above-described procedure, the measuring instrument without the liquid-retaining member (i.e., the stimulable phosphor member) can be subjected to the read-out operation by separating the liquid-retaining member therefrom prior to the read-out operation.

In the case of the separated sheet-form measuring instrument, the detection of a radioactive substance in a liquid sample can be carried out in the same manner as described on the integrated one, except that the stimulable phosphor member and liquid-retaining member of the instrument are used independently of each other.

FIG. 4 schematically illustrates an embodiment of a radiation-measuring system employing the separated instrument for detecting a radioactive substance present in a sample which is allowed to drop continuously.

In a sample-introducing (sample-depositing) section 62, a liquid sample 64 is allowed to drop from the bottom of a sample supplier 63 on a liquid-retaining support medium 61 which is one member of the integrated measuring instrument. While the support medium 61 is moved in the direction of arrows X and Y as afore-mentioned, the sample is deposited in a continuous or discontinuous band form on the support medium 61, adsorbed and held by the liquid-retaining layer thereof.

In a radiation energy-storage section 66, the liquid-retaining support medium 61 holding the sample and a stimulable phosphor sheet 65 which is another member of the integrated measuring instrument are placed together in layers, and at least a portion of the radiation energy emitted by a radioactive substance in the sample is absorbed by the stimulable phosphor sheet 65 and stored therein.

The stimulable phosphor sheet 65 storing the radiation energy is then separated from the liquid-retaining support medium 61, and is irradiated with stimulating rays 69 radiating from a light source 68 in a read-out section 67. Thus, the intensity of the radioactivity of the radioactive substance is determined in the same manner as described above.

In the operation for depositing the liquid sample continuously supplied from the sample supplier on the sheet-form radiation-measuring instrument, the moving method of the measuring instrument is not limited to the go-and-back movement in conjunction with of the shift movements in the X- and Y-directions as mentioned before, but other suitable methods may be also used. For example, the measuring instrument may be horizontally rotated with causing continuous slight shift of its center. In this case, the sample is adsorbed and held in a swirl form on the measuring instrument.

In the above-mentioned embodiments, the operation for reading out the radiation energy of the sample stored in the respective radiation-measuring instruments containing the stimulable phosphor has been described in some detail, but it will be understood that modifications can be made and another operation than that exemplified above can be used. Further, the raidation-measuring instrument employed in the present invention are by no means limited to those described above, and the methods of the invention can be carried out using other types of measuring instruments, provided that the instrument containing a stimulable phosphor retains a liquid sample continuously and absorbs radiation energy from the sample to give stimulated emission under irradiation with stimulating rays.

For example, it is possible that the sample portions in the measuring containers (or the sample deposited on the parts) from which detection of the radioactive substance is expected on the basis of the known data are only collected, whereby efficiently separating the desired radioactive substance. In the case of using the continuous-length measuring instrument, the sample portions from which detection of the radioactive substance is expected can be collected so that the aimed radioactive substance is efficiently separated, before the sample-deposited measuring instrument is wound up.

Further, the measuring procedure can be wholly automated by controlling the continuous operations comprising the introducing operation of the sample into the measuring instrument, storing operation of the radiation energy in the instrument, and the read-out operation of the instrument.

The used radiation-measuring instrument can be re-used by washing it with an appropriate solvent and irradiating it with light to erase the remaining energy. Therefore, the instrument can be continuously re-used by incorporating the washing operation of the used instrument and the erasing operation of the remaining energy after read-out operation in the process of the measuring procedure to automate the measuring procedure.

Alternatively, the read-out operation in the method of the present invention can be conducted for the measuring instrument from which the sample has been eliminated, so that the read-out operation of stimulated emission from the instrument can be easily conducted with high accuracy, for example, in the case that the sample is colored.

The method of detecting radioactive substance of the present invention is applied to liquid samples supplied continuously such as liquid samples separated and developed in a column in the liquid chromatography. Especially, the method using the plural measuring containers with the built-in stimulable phosphor is advantageously employed in the case that a large amount of the liquid sample is involved. The method using the continuous-length measuring instrument or the sheet-form measuring instrument is advantageously employed in the case that a small amount of the liquid sample is involved. The radioactive substances in the samples are sequentially detected with high efficiency and in a short time, and can be separated and identified with high accuracy.

I claim:

1. A method of detecting radioactive substance in a liquid sample which comprises the steps of:
   (1) supplying a radiation-measuring instrument having a stimulable phosphor covered with a polymer material with the liquid sample continuously or intermittently;
   (2) keeping said measuring instrument in contact with the liquid sample for a given period of time to cause the instrument to absorb at least a portion of radiation energy emitted by the radioactive substance in said liquid sample; and
   (3) irradiating said measuring instrument with an electromagnetic wave to release the radiation energy stored in the instrument as stimulated emission, and photoelectrically detecting the stimulated emission to measure radioactivity of said liquid sample sequentially.

2. The method of detecting radioactive substance as claimed in claim 1, wherein the liquid sample is a liquid containing a radioactive substance and being treated by liquid chromatography.

3. The method of detecting radioactive substance as claimed in claim 1, wherein the content of the radioactive substance in the liquid sample is measured.

4. The method of detecting radioactive substance as claimed in claim 1, wherein the stimulable phosphor is a divalent europium activated alkaline earth metal fluorohalide phosphor.

5. The method of detecting radioactive substance as claimed in claim 1, wherein the stimulable phosphor is a rare earth element activated rare earth oxyhalide phosphor.

6. A method of detecting radioactive substance in a liquid sample treated in liquid chromatography which comprises steps of:
   (1) sequentially setting a plurality of measuring containers having a stimulable phosphor covered with a polymer material under a sample supplier containing a liquid sample, and supplying said liquid sample continuously or intermittently into said measuring containers from the sample supplier;
   (2) keeping each of said plurality of measuring containers in contact with the liquid sample for a given period of time to cause the container to absorb at least a portion of radiation energy emitted by the radioactive substance in said liquid sample; and
   (3) irradiating each of said plurality of measuring containers with an electromagnetic wave to release the radiation energy stored in the container as stimulated emission, and photoelectrically detecting the stimulated emission to measure radioactivity of said liquid sample sequentially.

7. The method of detecting radioactive substance as claimed in claim 6, wherein the measuring container has a built-in stimulable phosphor being dispersed in a binder.

8. The method of detecting radioactive substance as claimed in claim 6, wherein the measuring container is a plastic container with a built-in stimulable phosphor.

9. The method of detecting radioactive substance as claimed in claim 6, wherein the measuring container is a glass or quartz container with a built-in stimulable phosphor.

10. The method of detecting radioactive substance as claimed in claim 6, wherein the stimulable phosphor is a divalent europium activated alkaline earth metal fluorohalide phosphor.

11. The method of detecting radioactive substance as claimed in claim 6, wherein the stimulable phosphor is a rare earth element activated rare earth oxyhalide phosphor.

12. A method of detecting radioactive substance in a liquid sample treated in liquid chromatography which comprises steps of:
   (1) moving a continuous-length measuring instrument having a stimulable phosphor covered with a polymer material along the lengthwise direction under a sample supplier containing a liquid sample, and supplying said liquid sample continuously or intermittently onto said measuring instrument from the sample supplier;
   (2) keeping said measuring instrument in contact with the liquid sample for a given period of time to cause the instrument to absorb at least a portion of radiation energy emitted by the radioactive substance in said liquid sample; and
   (3) irradiating said measuring instrument with an electromagnetic wave to release the radiation energy stored in the instrument as stimulated emission, and photoelectrically detecting the stimulated emission to measure radioactivity of said liquid sample sequentially.

13. The method of detecting radioactive substance as claimed in claim 12, wherein the continuous-length measuring instrument is a plastic tape containing a stimulable phosphor therein.

14. The method of detecting radioactive substance as claimed in claim 12, wherein the continuous-length measuring instrument has a liquid-adsorbing ability.

15. The method of detecting radioactive substance as claimed in claim 12, wherein the continuous-length measuring instrument is a yarn or fabric made of a plastic fiber containing a stimulable phosphor therein.

16. The method of detecting radioactive substance as claimed in claim 12, wherein the continuous-length measuring instrument is a yarn or fabric made of a glass fiber containing a stimulable phosphor therein.

17. The method of detecting radioactive substance as claimed in claim 12, wherein the stimulable phosphor is a divalent europium activated alkaline earth metal fluorohalide phosphor.

18. The method of detecting radioactive substance as claimed in claim 12, wherein the stimulable phosphor is a rare earth element activated rare earth oxyhalide phosphor.

19. A method of detecting radioactive substance in a liquid sample treated in liquid chromatography which comprises steps of:
   (1) moving a sheet-form measuring instrument in the direction along the sheet-plane under a sample supplier containing a liquid sample, said measuring instrument comprising a stimulable phosphor member containing a stimulable phosphor therein, a transparent polymer film, and a liquid-retaining member provided in order, and supplying said liquid-retaining member of the measuring instrument from the sample supplier;
   (2) keeping said liquid-retaining member of the measuring instrument in contact with the liquid sample for a given period of time to cause the stimulable phosphor member thereof to absorb at least a portion of radiation energy emitted by the radioactive substance in said liquid sample; and
   (3) irradiating said measuring instrument with an electromagnetic wave to release the radiation energy stored in the instrument as stimulated emission, and photoelectrically detecting the stimulated emission to measure radioactivity of said liquid sample sequentially.

20. The method of detecting radioactive substance as claimed in claim 19, wherein the sheet-form measuring instrument is in a quadrangular form, and in the step (1), the movement of said measuring instrument is done in such a manner that the instrument moves by mutual repetition of going to and from along one side of the quadrangular in conjunction with a shift in the direction perpendicular being arranged therebetween.

21. The method of detecting radioactive substance as claimed in claim 19, wherein the liquid-retaining member of the sheet-form measuring instrument has a porous structure.

22. The method of detecting radioactive substance as claimed in claim 19, wherein the stimulable phosphor member of the sheet-form measuring instrument comprises a binder and a stimulable phosphor dispersed therein.

23. The method of detecting radioactive substance as claimed in claim 19, wherein the stimulable phosphor is a divalent europium activated alkaline earth metal fluorohalide phosphor.

24. The method of detecting radioactive substance as claimed in claim 19, wherein the stimulable phosphor is a rare earth element activated rare earth oxyhalide phosphor.

25. A method of detecting radioactive substance in a liquid sample treated in liquid chromatography which comprises steps of:
   (1) moving a sheet-form liquid-retaining member in the direction along the sheet-plane under a sample supplier containing a liquid sample, and supplying said liquid sample continuously or intermittently onto said liquid-retaining member from the sample supplier;
   (2) placing said liquid-retaining member carrying the liquid sample on a sheet-form stimulable phosphor member having a stimulable phosphor covered with a polymer material for a given period of time to cause the stimulable phosphor member to absorb at least a portion of radiation energy emitted by the radioactive substance in said liquid sample; and
   (3) irradiating said stimulable phosphor member with an electromagnetic wave to release the radiation energy stored in the stimulable phosphor member as stimulated emission, and photoelectrically detecting the stimulated emission to measure radioactivity of said liquid sample sequentially.

26. The method of detecting radioactive substance as claimed in claim 25, wherein the liquid-retaining member is in a quadrangular form, and in the step (1), the movement of said liquid-retaining member is done in such a manner that the member moves by mutual repetition of going to and from along one side of the quadrangle in conjunction with a shift in the direction perpendicular being arranged therebetween.

27. The method of detecting radioactive substance as claimed in claim 25, wherein the liquid-retaining member has a porous structure.

28. The method of detecting radioactive substance as claimed in claim 25, wherein the stimulable phosphor sheet comprises a binder and a stimulable phosphor dispersed therein.

29. The method of detecting radioactive substance as claimed in claim 25, wherein the stimulable phosphor is a divalent europium activated alkaline earth metal fluorohalide phosphor.

30. The method of detecting radioactive substance as claimed in claim 25, wherein the stimulable phosphor is a rare earth element activated rare earth oxyhalide phosphor.

* * * * *